(12) United States Patent
Letort

(10) Patent No.: US 8,048,409 B2
(45) Date of Patent: Nov. 1, 2011

(54) CELLULAR THERAPY TO HEAL VASCULAR TISSUE

(75) Inventor: Michel Letort, Prevessins (FR)

(73) Assignee: Medtronic Vascular, Inc., Santa Rosa, CA (US)

( * ) Notice: Subject to any disclaimer, the term of this patent is extended or adjusted under 35 U.S.C. 154(b) by 1917 days.

(21) Appl. No.: 10/911,198

(22) Filed: Aug. 4, 2004

(65) Prior Publication Data

US 2005/0276864 A1    Dec. 15, 2005

Related U.S. Application Data

(60) Provisional application No. 60/575,046, filed on May 27, 2004.

(51) Int. Cl.
    *A01N 63/00*    (2006.01)
    *A01N 65/00*    (2009.01)
    *A61F 2/06*     (2006.01)

(52) U.S. Cl. ............... 424/93.1; 424/93.2; 623/1.41

(58) Field of Classification Search ............... 424/93.1, 424/93.2; 623/1.41
See application file for complete search history.

(56) References Cited

U.S. PATENT DOCUMENTS

| | | | |
|---|---|---|---|
| 5,486,359 A | 1/1996 | Caplan et al. | 424/93.7 |
| 5,538,504 A | 7/1996 | Linden et al. | 604/53 |
| 5,670,161 A | 9/1997 | Healy et al. | 623/1.42 |
| 6,096,347 A | 8/2000 | Geddes et al. | 424/551 |
| 6,143,293 A | 11/2000 | Weiss et al. | 424/93.7 |
| 6,151,525 A | 11/2000 | Soykan et al. | 607/50 |
| 6,159,239 A | 12/2000 | Greenhalgh | 623/1.13 |
| 6,190,353 B1 | 2/2001 | Makower et al. | 604/95.01 |
| 6,302,870 B1 | 10/2001 | Jacobsen et al. | 604/272 |
| 6,344,035 B1 | 2/2002 | Chudzik et al. | 604/265 |
| 6,348,050 B1 | 2/2002 | Hartlaub | 604/891.1 |
| 6,364,903 B2 | 4/2002 | Tseng et al. | 623/1.15 |
| 6,368,346 B1 | 4/2002 | Jadhav | 623/1.22 |
| 6,371,970 B1 | 4/2002 | Khosravi et al. | 606/200 |
| 6,376,742 B1 | 4/2002 | Zdrahala et al. | 623/11.11 |
| 6,387,121 B1 | 5/2002 | Alt | 3/1.15 |
| 6,429,013 B1 | 8/2002 | Halvorsen et al. | 435/377 |
| 6,451,373 B1 | 9/2002 | Hossainy et al. | 427/2.25 |
| 6,497,875 B1 | 12/2002 | Sorrell et al. | 424/93.7 |
| 6,506,410 B1 | 1/2003 | Park et al. | 424/489 |
| 6,514,515 B1 | 2/2003 | Williams | 424/424 |
| 6,531,154 B1 | 3/2003 | Mathiowitz | 424/487 |
| 2002/0065546 A1 | 5/2002 | Machan et al. | 623/1.13 |

FOREIGN PATENT DOCUMENTS

WO     0215824     2/2002

OTHER PUBLICATIONS

Conclaves M, A concise peer into the background, initial thoughts, and practices of human gene therapy, 2005, BioEssays, vol. 27, pp. 506-517.*
Verma IM, Gene Therapy: Twenty-first century medicine, 2005, Annu. Rev. Biochem. vol. 74, pp. 711-738.*
Parekh-Olmedo H, Gene therapy progress and prospects: targeted gene repair, 2005, Gene Therapy, vol. 12, pp. 639-646.*
2008, Saric et al., Cells Tissues Organs, vol. 188, pp. 78-90 (Web-Printed Abstract Provided).*
2006, Grinnemo et al., RBM Online, vol. 13(5), pp. 712-714.*
2008, Grinnemo et al., Cell Tissue Res., vol. 331, pp. 67-78.*
2005, Martin et al., Nature Medicine, vol. 11(2), pp. 228-232.*
Herzog et al., 2003, Blood, vol. 102(10), pp. 3483-3493.*
Pittenger et al., 2004, Circ. Res., vol. 95, pp. 9-20.*
Guillot et al., 2007, J. Cell. Mol. Med., vol. 11(5), pp. 935-944.*
Lakshmipathy et al., 2005, Blood Rev., vol. 19, pp. 29-38.*
Naito, H., et al., Heart Surg. Forum, 6(1): 1 (2002).
Oshima, H., et al., Heart Surg. Forum, 6(1): 7 (2002).
Min, J.Y., et al, J. Thorac. Cardiovasc. Surg., 125(2): 361-69 (2003).
Chiu, R., et al., Ann. Thorac, Surg., 60:12-18 (1995).
Gulbins, H., et al., Heart Surg. Forum, 5(4): 28 (2002).
Rohrich, et al., Plastic and Reconstructive Surgery, 99:514-19 (1997).
Noishiki, et al., Artificial Organs, 25(3): 228-35 (2001).
Zuk, et al., Tissue Engineering, 7(2): 211-28.
Simper, et al., Circulation, 106: 1199-1204 (2002).
Yablonka-Reuveni and Nameroff, Histochemistry, 87: 27-38 (1987).
Maniatis, Fritsch & Sambrook, Molecular Cloning: A Laboratory Manual (1982).
DNA Cloning: A Practical Approach, vols. I and II (D.N. Glover, ed. 1985).
Ochoa and Vacanti, Ann. N.Y. Acad. Sci., 979:10-26 (2002).
Chaikof, et al., Ann. N.Y. Acad. Sci., 961:96-105 (2002).
Griffith, Ann. N.Y. Acad. Sci., 961:83-95 (2002).
Goodman & Gilman's "The Pharmacological Basis of Therapeutics," $10^{th}$ Edition (2001).
Zhao et al., www.pnas.org/cgi/doi/10.1073/pnas.0536882100, vol. 100, No. 5, 2426-2431 (2003).
The Lancet, vol. 358, pp. 475 (Aug. 2001).
Liechty et al., Nature Medicine, vol. 6, No. 11 pp. 1282-1286 (Nov. 2000).
Toma, et al., Nature Cell Biology, vol. 3, pp. 778-784, http://cellbio.nature.com, (Sep. 2001).
Jiang et al., Nature, vol. 418, pp. 41-49, www.nature.com/nature/nature, (Jul. 2002).
Oishi, et al., Journal of Physiology, 540.1, pp. 139-152.
US 6,348,062, 02/2002, Hopkins et al. (withdrawn)

* cited by examiner

*Primary Examiner* — Peter Paras, Jr.
*Assistant Examiner* — David A Montanari

(57) ABSTRACT

The present invention encompasses methods and apparatus for minimizing the risks inherent in endovascular grafting for blood vessel therapy and repair. The invention involves delivering adult stem cells, embryonic stem cells, progenitor cells, fibroblasts, or smooth muscle cells to the diseased blood vessel, in some embodiments in conjunction with a stent graft.

30 Claims, 4 Drawing Sheets

CELLULAR THERAPY TO HEAL VASCULAR TISSUE

RELATED APPLICATIONS

This application claims the benefit of U.S. Provisional Patent Application 60/575,046 filed May 27, 2004.

BACKGROUND OF THE INVENTION

Aortic aneurysms and degeneration of the vasculature in general represent a significant medical problem for the general population. Aneurysms within the aorta presently affect between two and seven percent of the general population and the rate of incidence appears to be increasing. This form of vascular disease is characterized by degeneration in the arterial wall in which the wall weakens and balloons outward. Until the affected artery is grafted through open repair or treated with a stent graft endovascularly, a patient with an aortic aneurysm must live with the threat of aortic aneurysm rupture and death.

One known clinical approach for patients with an aortic aneurysm is a surgical repair procedure. This is an extensive operation involving dissection of the aorta and reinforcement of the aneurysm wall with a prosthetic graft.

Alternatively, there is a significantly less invasive clinical approach to aneurysm repair known as endovascular grafting. Endovascular grafting involves the placement of a prosthetic arterial stent graft within the lumen of the artery. To prevent rupture of the aneurysm, a stent graft of tubular construction is introduced into the blood vessel, and is secured in a location such that the stent graft spans the length of the aneurysmal sac. The outer surface of the stent graft at its ends is sealed to the interior wall of the blood vessel at a location where the blood vessel wall has not suffered a loss of strength or resiliency, such that blood flowing through the vessel is diverted through the hollow interior of the stent graft away from the blood vessel wall at the aneurysmal sac location. In this way, the risk of rupture of the blood vessel wall at the aneurysmal location is reduced significantly and blood can continue to flow through to the downstream blood vessels without interruption. However, despite the advantages of endovascular grafting over other surgical procedures, there may be, nonetheless, continued progression of the aneurysm.

A salient feature of aneurysm formation is the gradual degradation of extracellular components, such as collagen and elastin, as well as the loss of resident cells. The cells in a healthy vessel perform many and varied functions, including providing reinforcement to the vessel wall and, importantly, replenishing the extracellular components. The diminished cellular presence observed in diseased arteries directly and adversely impacts the vessel wall ultrastructure.

Thus there is a desire in the art to slow, reverse, or cure the aneurysm disease state by using minimally invasive procedures while reducing or eliminating immunological rejection.

SUMMARY OF THE INVENTION

The present technology addresses the problem of degeneration of vascular tissue, particularly at an aneurysmal site. Embodiments according to the present invention provide methods for supporting and treating the vascular tissue with skeletal myoblasts or myocytes from embryonic or adult stem cell sources. Such cells function to regenerate, reinforce and strengthen the disease site.

Thus, in one embodiment, there is provided a method of treating a blood vessel in an individual comprising: harvesting tissue; isolating cells from the harvested tissue; and delivering the isolated cells to an aneurysmal site in the blood vessel by a delivery means. In one aspect, single cell populations or combination cell populations (which include more than one cell type) are used. In another aspect of this embodiment, the isolated cells are expanded or differentiated in vitro before delivery. In another aspect of an embodiment, the cells are genetically engineered in vitro before delivery. In another aspect of an embodiment, the cells are delivered in conjunction with a carrier and/or cellular scaffold and are left to expand, and, if necessary, differentiate in vivo. In yet another aspect of the embodiment, the cells are delivered together with agents, such as growth factors, to promote or enhance cell proliferation and/or secretion in vivo.

Thus, the present invention in one embodiment provides a method of providing therapy to a blood vessel wall at an aneurysmal site, comprising: harvesting tissue; isolating myocytes from the tissue; and delivering the myocytes to the blood vessel wall at the aneurysmal site by delivery means. The harvesting step may be accomplished by liposuction, drawing blood, harvesting bone marrow, or isolating an inner cell mass of a preimplantation embryo. In another embodiment, there is provided a method of providing therapy to a blood vessel wall at an aneurysmal site in an individual, comprising: harvesting skeletal muscle tissue from the individual; isolating at myoblasts from the tissue; and delivering the myoblasts to the blood vessel wall at the aneurysmal site by delivery means.

The methods according to the present invention may further comprise the step of modifying the myocytes or myoblasts after the isolating step. For example, the modifying step may be accomplished by genetic engineering; such as by genetically engineering the myocytes or myoblasts to produce at least one cellular factor selected from the group of collagen I, collagen III, elastin, cytokines, growth factors, metalloproteinase inhibitors, inhibitors of inflammation, vitamin A, vitamin C, angiogenic factors or any other factor found in healthy vessel. Alternatively or in addition, the myocytes or myoblasts may be expanded, combined or differentiated subsequent to the isolation step. Also, myocytes or myoblasts may be combined with a scaffolding and/or a carrier compound prior to delivery.

BRIEF DESCRIPTION OF THE DRAWINGS

A more particular description of the invention, briefly summarized above, may be had by reference to the embodiments of the invention described in the present specification and illustrated in the appended drawings

DETAILED DESCRIPTION

Reference will now be made in detail to exemplary embodiments according to the invention.

The present technology encompasses methods for treating the wall of blood vessels in an aneurysmal site in an individual. Aspects according to the invention include a method for delivering myocytes, preferably from adult stem cells, derived from, for example, adipose tissue, bone marrow, or peripheral blood of an individual, to a blood vessel in need of therapy. Alternatively, the myocytes can be from embryonic stem cells isolated from the inner cell mass of preimplantation embryos. Also included are methods for the delivery of skeletal myoblasts (satellite cells), derived from skeletal muscle. The skeletal myoblasts or myocytes (derived from adult or embryonic sources) to be delivered may come directly from the skeletal muscle, adipose tissue, bone marrow, or other tissue samples, or the cells may be cultured, expanded, combined or manipulated before delivery. One cell type or a combination of cell types may be delivered. In addition, the cells may be delivered along with a natural or synthetic cellular scaffolding material and/or carrier solution, and with or without bioactive agents.

Figure 1:
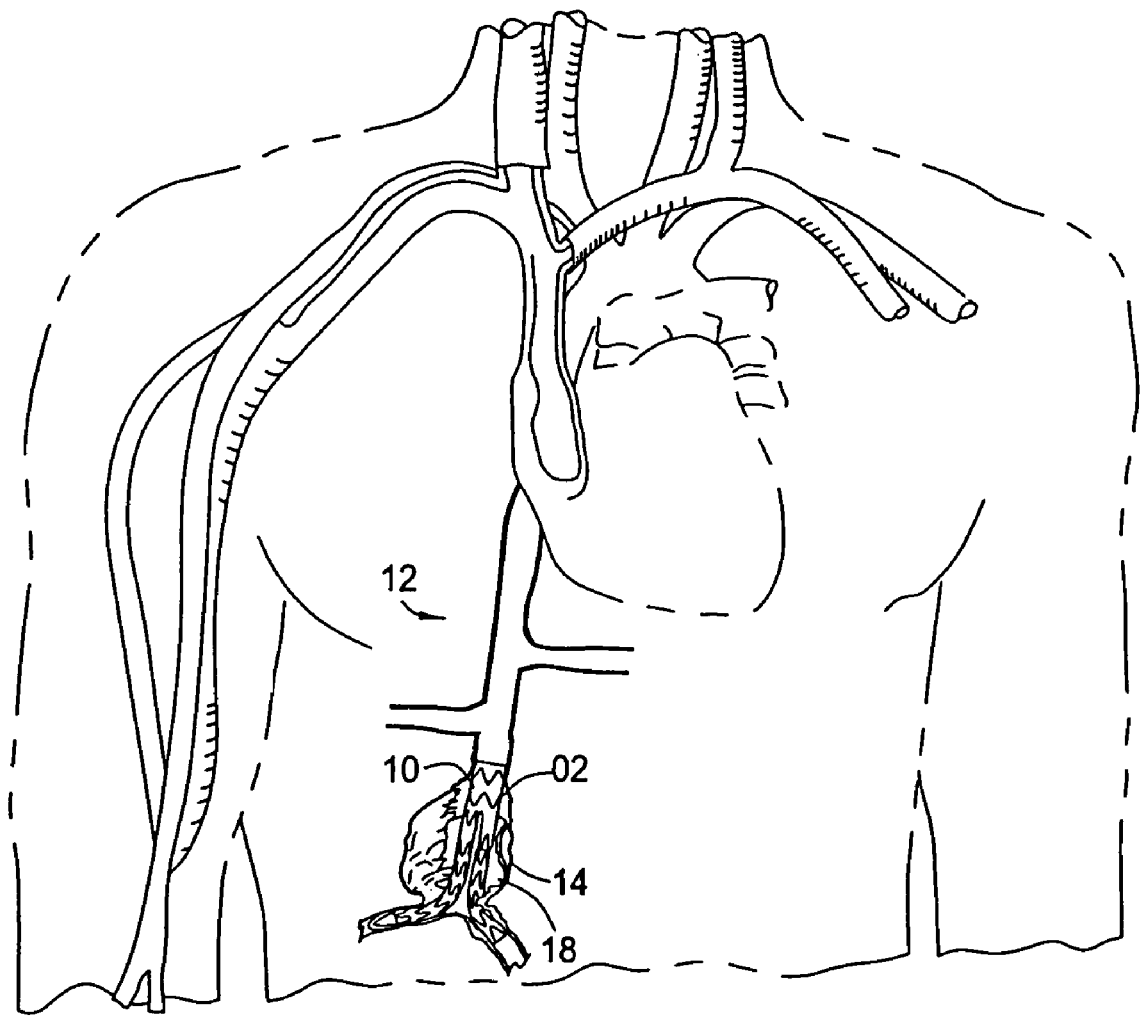
FIG. 1 is a schematic view of a human aortal aneurysm.

Referring initially to FIG. 1, there is shown generally an aneurysmal blood vessel; in particular, there is an aneurysm of the aorta 12, such that the aorta or blood vessel wall 04 is enlarged at an aneurysmal site 14 and the diameter of the aorta 12 at the aneurysmal site 14 is larger than the diameter of a healthy aorta 12. The aneurysmal site 14 forms an aneurysmal bulge or sac 18. If left untreated, the aneurysmal sac 18 may continue to deteriorate, weaken, increase in size, and eventually tear or burst.

As stated previously, vascular surgery and endovascular grafts have proven successful in patients with aortic aneurysms; however, neither procedure inhibits the progression of the disease state. Before the aneurysm reaches a size to necessitate such procedures, embodiments according to the present invention treats blood vessels directly—at the site of an aneurysm—possibly preventing the need for subsequent surgical repair. Alternatively, this technology can be used in addition to surgery or placement of a stent graft to bolster and provide enhanced healing at the aneurysmal site. The methods involve tissue engineering using self-derived cells such as skeletal myoblasts (satellite cells) or adult stem cell-derived myocytes, or, alternatively, immuno-neutral non-self-derived stem cells, such as embryonic stem cell-derived myocytes.

Progression of the disease state is characterized by continued degeneration of the aortic wall due to thinning of the medial connective tissue architecture (mostly due to degradation of elastin, then collagen) of the aorta, and a concomitant loss of collagen in the adventitia associated with dilatation of the vessel. There is evidence that connective tissue-degrading enzymatic activity is triggered by inflammation in the medial and adventitial layers of the aorta. Accordingly, one aspect of one embodiment of the present invention involves limiting the spread of inflammation by implantation of skeletal myoblasts or myocytes from embryonic or adult stem cells into the blood vessel wall such that the newly-created muscle bolsters the aneurysmal site while exerting a paracrine, protective effect against artery wall destruction by inflammation. The muscle cells in this in vivo setting thus are likely to secrete extracellular components that increase the health of the surrounding tissue. Thus, among other advantages, this embodiment provides the blood vessel with therapy that protects and regenerates extracellular matrix components in the medial and adventitial layers of blood vessels, preventing continued dilatation and/or further degeneration of the aortic tissue.

It has been reported that bone marrow-derived adult stem cells, embryonic stem cells and myoblasts have been used to grow new muscle and blood vessels in heart tissue that has been damaged following myocardial infarction in mice, dogs and rats (see, e.g., Naito, H., et al., *Heart Surg. Forum,* 6(1): 1 (2002); Oshima, H., et al., *Heart Surg. Forum,* 6(1): 7 (2002); Min, J. Y., et al, *J. Thorac. Cardiovasc. Surg.,* 125(2): 361-69 (2003); Chiu, R., et al., *Ann. Thorac, Surg.,* 60: 12-18 (1995); and Gulbins, H., et al., *Heart Surg. Forum,* 5(4): 28 (2002)). In these instances, remodeling of the cardiac tissue was observed, with an increase of vascularization of the infarct region. Embodiments according to the present invention are drawn to methods of using such cells to address the problems associated with aneurysmal tissue.

Cells suitable for implantation in the present invention include skeletal myoblasts and myocytes from embryonic and adult stem cells. Typically, these differentiate to form muscle cells, however, they can be fibroblasts that have been converted to myoblasts ex vivo, or any of a wide variety of immunologically neutral cells that have been programmed to function as undifferentiated contractile cells. The cells can be genetically engineered or nonengineered. Mixtures of such cells also can be used. Autologous cells are particularly desirable.

Skeletal muscle satellite cells are particularly suitable for use because they can differentiate to muscle cells. They are also particularly suitable for use because they can be obtained from cell cultures derived from the biopsy samples of the same patient. Biopsy samples contain mature skeletal fibers along with reserve cells surrounding the mature fibers. Once placed in culture as described in the Example section infra, reserve cells proliferate and their numbers quickly increase. These newly cultured cells are then implanted at the aneurysmal site.

Figure 2:
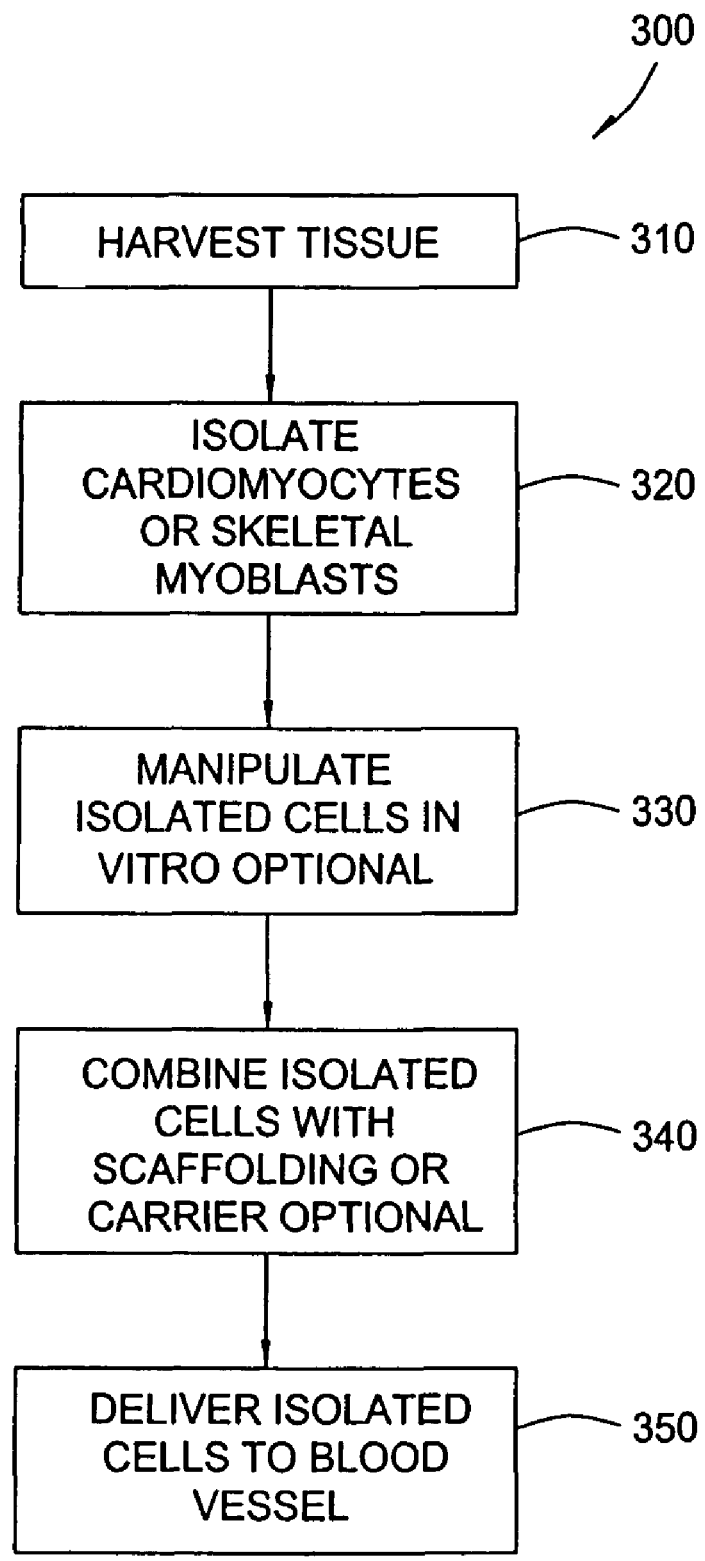
FIG. 2 is a flow chart of one embodiment of the methods according to the present invention.

FIG. 2 is a flow chart of one embodiment of methods according to the present invention. In FIG. 2, method 300 is comprised of three main steps and two optional steps. In step 310, tissue is harvested from, for example, adipose tissue, bone marrow, blood or other tissues where adult stem cells may be found or skeletal muscle where skeletal myocytes are found or embryos where embryonic stem cells are found. For example, adipose tissue is readily accessible and abundant in most individuals and can be harvested by liposuction. Various liposuction techniques exist, including ultrasonic-assisted liposuction ("UAL"), laser-assisted liposuction, and traditional suction-assisted liposuction ("SAL"), where fat is removed with the assistance of a vacuum created by either a mechanical source or a syringe. Each of the foregoing liposuction techniques may be used in conjunction with tumescent solution. Liposuction procedures that use a tumescent solution generally involve pre-operative infiltration of subcutaneous adipose tissue with large volumes of dilute anesthetic solutions. The evolution of the tumescent technique has revolutionized liposuction by making it available on an outpatient basis. Specifically, it makes the use of general anesthesia optional in most cases thereby avoiding the associated risks and costs. (See, e.g., Rohrich, et al., *Plastic and Reconstructive Surgery,* 99:514-19 (1997).)

Another advantage of using adipose tissue as a source of adult stem cells is that, due to the abundance of stem cells in adipose tissue, stem cell harvest, isolation, genetic manipulation and/or growth-factor based differentiation may be accomplished peri-operatively. Thus, depending on the number of cells required for implantation, it may not be necessary for the patient to submit to the liposuction procedure on one day and the stem cell implantation on a subsequent day. The procedures can be performed sequentially within minutes or tens of minutes of one another. (See, e.g., Noishiki, et al., *Artificial Organs,* 25(3): 228-35 (2001); and Zuk, et al., *Tissue Engineering,* 7(2): 211-28).

Alternatively, bone marrow may be harvested for adult stem cells. As a whole, bone marrow is a complex tissue comprised of two distinct populations of stem cells, namely hematopoietic stem cells and mesenchymal stem cells.

Hematopoietic stem cells give rise to components of the blood and immune systems while mesenchymal stem cells give rise to varied cells, including osteoblasts, chondrocytes, adipocytes, fibroblasts, smooth muscle cells, and myoblasts. Cells, such as fibroblasts, reticulocytes, adipocytes and endothelial cells, form a connective tissue network called "stroma". Cells from the stroma regulate morphologically the differentiation of hematopoietic cells through direct interaction via cell surface proteins and the secretion of growth factors. Stroma cells also are involved in the foundation and support of the bone structure. Studies using animal models show that bone marrow contains "pre-stromal" cells which have the capacity to differentiate into cartilage, bone, and other connective tissue cells, and, in an inverse relationship with age, they are capable of differentiating into an assortment of connective tissues depending upon the influence of a number of bioactive factors. While mesenchymal stem cells are extremely rare in bone marrow, they also can be found in other tissues, such as peripheral blood, umbilical cord blood and adipose tissue.

In certain embodiments according to the present invention, an autologous bone marrow transplant is contemplated. In an autologous transplant, the individual to receive therapy donates his or her own stem cells for later reinfusion. The procedure for harvesting bone marrow from the individual is performed while the individual is under anesthesia. A needle is inserted into the cavity of the rear hip bone, the iliac crest, where a large quantity of bone marrow is located. The bone marrow is a thick, red liquid and is extracted by a syringe. Several skin punctures on each hip and multiple bone punctures may be required to harvest enough stem cells for use in embodiments according to the present invention.

In yet another embodiment, adult stem cells may be derived from peripheral blood. Human blood has circulating adult progenitor cells that are capable of differentiating into muscle-like cells in response to platelet derived growth factor (PDGF-BB) treatment. (See, e.g., Simper, et al., *Circulation*, 106: 1199-1204 (2002)). Thus, in one embodiment of the present invention, a blood draw is contemplated. Since progenitor cell populations are present in blood in very low percentages, the cells are expanded in culture following growth factor-induced differentiation and selection. Alternatively, the patients may be systemically treated with agents, such as granulocyte-colony stimulating factor (G-CSF), granulocyte monocyte colony-stimulating factor (GM-CSF), or the like, which are known to increase hematopoietic progenitors in humans by activating and promoting mobilization of these progenitors from bone marrow into the circulation by several fold.

Skeletal myoblasts can be isolated from skeletal muscle, from the individual to be treated, thus circumventing any issues associated with immuno-rejection, or can be isolated from skeletal muscle of another individual. A technique describing the isolation of skeletal myoblasts from the tibialis anterior muscle is described in the Example section herein.

In a next step, step 320 of FIG. 2, cells are isolated from the harvested tissue. In general, methods of isolation of cells includes not only harvesting a tissue specimen, but also processing the specimen so that the cells contained therein are substantially dissociated into single cells rather than grouped as cell clusters. Dissociating the cells into single cell components can be accomplished by any method known in the art; e.g., by mechanical (filtering) or enzymatic means. Further, the isolating step includes combining the cell-containing specimen with a cell culture medium comprising factors that (i) stimulate cell growth without differentiation, and (ii) allow expansion of substantially only the myocytes or myoblasts. Next, the specimen-medium mixture is cultured for a few up to many cell passages.

Protocols for the identification of myocytes or myoblasts are well established. Markers that can be monitored and selected for in myocytes include α-cardiac myosin heavy chain (α-MHC), myasin light chain isoform 2V, NKX2.5, Myf5, myogenin, MyoD, Myf6, and M-Cadherin. Selection can be accomplished by fluorescence activated cell sorting (FACS), magnetic activated cell sorting (MACS), western blotting, or by other techniques known by those skilled in the art. Skeletal myoblasts can be purified substantially by density centrifugation according to the method of Yablonka-Reuveni and Nameroff, *Histochemistry*, 87: 27-38 (1987).

Step 330 shown in FIG. 2 allows for the option of modifying the myocytes or myoblasts, such as genetically altering or engineering the cells or expanding the cell population in vitro. Methods for genetic engineering or modifying cells are known to those with skill in the art (see, generally, Maniatis, Fritsch & Sambrook, *Molecular Cloning: A Laboratory Manual* (1982); and *DNA Cloning: A Practical Approach, Volumes I and II* (D. N. Glover, ed. 1985)). To genetically engineer the myocytes or myoblasts, the myocytes or myoblasts may be stably or transiently transfected or transduced with a nucleic acid of interest using a plasmid, viral or alternative vector strategy. Nucleic acids of interest include, but are not limited to, those encoding gene products that produce or enhance the production of extracellular matrix components found in the blood vessel wall such as cytokines or growth factors, factors that enhance vascular health and elasticity such as proteolytic inhibitors, or biological response modulators such as ascorbic acid (vitamin C) or retinoic acid (vitamin A) that alter the secretory properties of fibroblasts and vascular smooth muscle cells to increase collagen type I and III and elastin production. For example, since tissue repair naturally occurs in an extracellular matrix environment rich in glycosamines and glycoproteins, in one embodiment, the myocytes or myoblasts are genetically engineered to produce one or more such compounds.

Alternatively or in addition, it has been shown that medial thinning and breakdown of elastin and collagen in the aorta is due, at least in part, to the effects of matrix metalloproteinases (MMPs). MMPs (MMP2, gelatinase A; MMP9, gelatinase B, and MMP 12, metalloelastase) are a group of proteolytic enzymes associated with the extracellular matrix. MMPs are known to degrade one or more connective tissue elements and have been implicated in clearing a path through the extracellular matrix for cell migration. Thus, in one aspect, the myocytes or myoblasts may be engineered to inhibit the progression of an established (pre-existing) aneurysm by, e.g., inhibiting MMPs. Suitable inhibitors may include, for example, endogenous inhibitors, such as tissue inhibitors of MMPs (TIMPs) and macroglobulins, and synthetic inhibitors, such as chelating agents (e.g., EDTA and 1,10-phenanthroline), peptides, antibodies, and antibiotics such as tetracycline and its derivatives.

The maximal dosage of a bioactive agent such as an MMP inhibitor in this context is the highest dosage of the bioactive agent that effectively inhibits elastolytic anti-aneurysmal activity, but does not cause undesirable or intolerable side effects. The practitioner is guided by skill and knowledge in the field, to include without limitation dosages that are effective to achieve the described phenomena.

The transduction of viral vectors carrying genes for bioactive compounds into the myocytes or myoblasts can be performed with viral vectors (adenovirus, retrovirus, adeno-associated virus, or other viral vectors) that have been isolated and purified. In such techniques, myocytes or myoblasts are exposed to the virus in serum-free media in the absence or presence of a cationic detergent for a period of time sufficient to accomplish the transduction.

Alternatively, vectors carrying genes for bioactive compounds can be introduced into the myocytes or myoblasts by use of calcium phosphate DNA precipitation, cationic detergent methods, liposomes, TAT-derived cell penetrating peptides, or in three-dimensional cultures by incorporation of the plasmid DNA vectors directly into a biocompatible polymer. Perioperative cell transfection may include ultrasound, magnetic field mediated-, or electorporation techniques. Electroporation protocols are known in the art and also can be found, e.g., in Maniatis, Fritsch & Sambrook, *Molecular Cloning: A Laboratory Manual* (1982); and *DNA Cloning: A Practical Approach, Volumes I and II* (D. N. Glover, ed. 1985). For the tracking and detection of functional proteins encoded by the introduced genes, the viral or plasmid DNA vectors can contain a readily detectable marker gene, such as green fluorescent protein or the beta-galactosidase enzyme, both of which can be tracked by histochemical means.

Another method for modifying the myocytes or myoblasts prior to delivery to the aneurysmal sac is to expand the cardiomyocyte or myoblast population. Basically, the expansion process is accomplished by prolonged in vitro culturing of the myocytes or myoblasts in the selective cell culture medium (i.e., the medium that stimulated cardiomyocyte or myoblast growth without differentiation) from several to many successive cell passages. On the other hand, because adipose tissue yields a relatively large number of stem cells, if adipose tissue is used as a source of myocytes, in vitro expansion typically is not necessary.

Step 340 of FIG. 2 is another optional step that provides combining the myocytes or myoblasts to be delivered to the blood vessel with a carrier or scaffold. Many strategies in tissue engineering have focused on the use of biodegradable polymers as temporary scaffolds for cell transplantation or tissue induction. The success of a scaffold-based strategy is highly dependent on the properties of the material, requiring at a minimum that it be biocompatible, easy to sterilize, and, preferably, degradable over an appropriate time scale into products that can be metabolized or excreted. Mechanical properties are also important in polymer scaffold design for the regeneration tissues such as connective tissue, adipose tissue or blood vessels. In addition, scaffold degradation rates should be optimized to match the rate of tissue regeneration. Ideally degradable scaffolding polymers should yield soluble, resorbable products that do not induce an adverse inflammatory response. Alternatively, biodegradable scaffolds fabricated from naturally occurring elements, such as collagen, fibrin, hyaluronic acid, with or without growth factors connected to the backbone can be used as cell carriers. For general information regarding tissue engineering, see Ochoa and Vacanti, *Ann. N.Y. Acad. Sci.*, 979:10-26 (2002); Chaikof, et al., *Ann. N.Y. Acad. Sci.*, 961:96-105 (2002); Griffith, *Ann. N.Y. Acad. Sci.*, 961:83-95 (2002); Weiss, et al., U.S. Pat. No. 6,143,293; and Zdrahala, et al., U.S. Pat. No. 6,376,742.

In addition to porous scaffolds, embodiments according to the present invention contemplate using a gel scaffold. Such gels may be synthetic or semisynthetic gels that may not only stimulate cells through inclusion of adhesion and/or growth factor moieties, but may also respond to cells by degrading in the presence of specific cell cues. In one particularly well-developed family of gels known in the art, the basic macromer unit is a linear or branched polyethylene oxide end-capped with chemically reactive groups. Such a gel is particularly flexible for use in embodiments according to the present invention as it is intrinsically non-adhesive for cells and the gel properties can be tailored: the consistency of the gel can be controlled by the size of the monomers and the gel thickness; controlled degradation may be had by including hydrolysable polyester segments or enzyme-cleavable peptides at the chain ends, and adhesion peptides can be included in the gel at a concentration to control cell interactions.

Another type of useful gel is a stimuli-responsive polymer gel. Stimuli-responsive polymer gels are compounds that can be triggered to undergo a phase-transition, such as a sol-gel transition. This property aids in reducing the pressure required to get the polymer-cell suspension through the delivery means. A preferred system would be a polymer-scaffolding system that is liquid at room temperature and gels at a temperature slightly below body temperature.

As described previously, myoblasts or myocytes respond to soluble bioactive molecules such as cytokines, growth factors, or other factors and can be engineered to secrete such factors as well as metalloproteinase inhibitors. Thus, these molecules alone can be used for tissue induction or growth. Alternatively, the tissue-inductive factors or MMP inhibitors can be incorporated into the biodegradable polymer of the scaffold, as an alternative to or in addition to engineering the myoblasts or myocytes to produce such inductive factors. In yet another alternative, biodegradable microparticles or nanoparticles loaded with these molecules can be embedded into the scaffold substrate.

Alternatively, embodiments of the present invention provide implanting myocytes or myoblasts along with the differentiation factors appropriate to induce muscle cell differentiation; however, if such factors are used they are preferably administered in a time release fashion.

Thus, the cells can be delivered with or without a cellular scaffolding or matrix element. However, in addition, the cells and scaffolding, if present, likely will be delivered in a pharmaceutically acceptable solution or diluent. For example, the cells may be delivered in a carrier of sterile water, normal saline, culture medium or other pharmaceutically acceptable carrier, alone or in combination with a pharmaceutically acceptable auxiliary substance, such as a pH adjusting or buffering agent, tonicity adjusting agent, stabilizer, wetting agent, and the like.

Alternate embodiments of this invention include encapsulating the cells in biodegradable microspheres or capsules, designed for gradual or measured release over time.

Referring again to FIG. 2, once myocytes or myoblasts have been isolated and/or expanded, they can be delivered to the blood vessel. To do so, several alternative delivery means may be employed. For example, syringes or microneedles may be used to deliver the stem cells directly to the wall of the blood vessel. Alternatively, catheters or other apparatus that function to deliver fluids into the walls of blood vessels may be employed. For example, Jacobsen, et al., U.S. Pat. No. 6,302,870, describe an apparatus for injecting fluids into the walls of blood vessels comprising a plurality of laterally-placed flexible needles disposed within a catheter. Similarly, Linden, et al., U.S. Pat. No. 5,538,504, describe a drug delivery catheter that comprises an elongated tubular shaft with a vessel puncturing element that remains retracted while the catheter is being deployed, and is then advanced to a protruding position at the site where the vessel is to be treated. Also, Makower, et al., U.S. Pat. No. 6,190,353, disclose a similar device for performing drug or other delivery procedures at specific locations in a blood vessel using a catheter comprising a deployable element that can penetrate the wall of the vessel.

As another alternative, the cells may be delivered through a wrap comprised of cells embedded within a matrix or scaffold, applied either periadventially or intralumenally. Alternatively, in order to promote the survival of transplanted cells, chronic cell delivery may be needed. In such an embodiment, programmable, refillable pumps may be employed to deliver cells, or cell compositions, that include bioactive agents to the affected region. As shown by Hartlaub, U.S. Pat. No. 6,348,050, pump-based infusion systems may be used to gradually monitor cells, together with the appropriate biological response modulators, to create and maintain the optimal microenvironment for ensuring cell survival and function.

Figure 3:
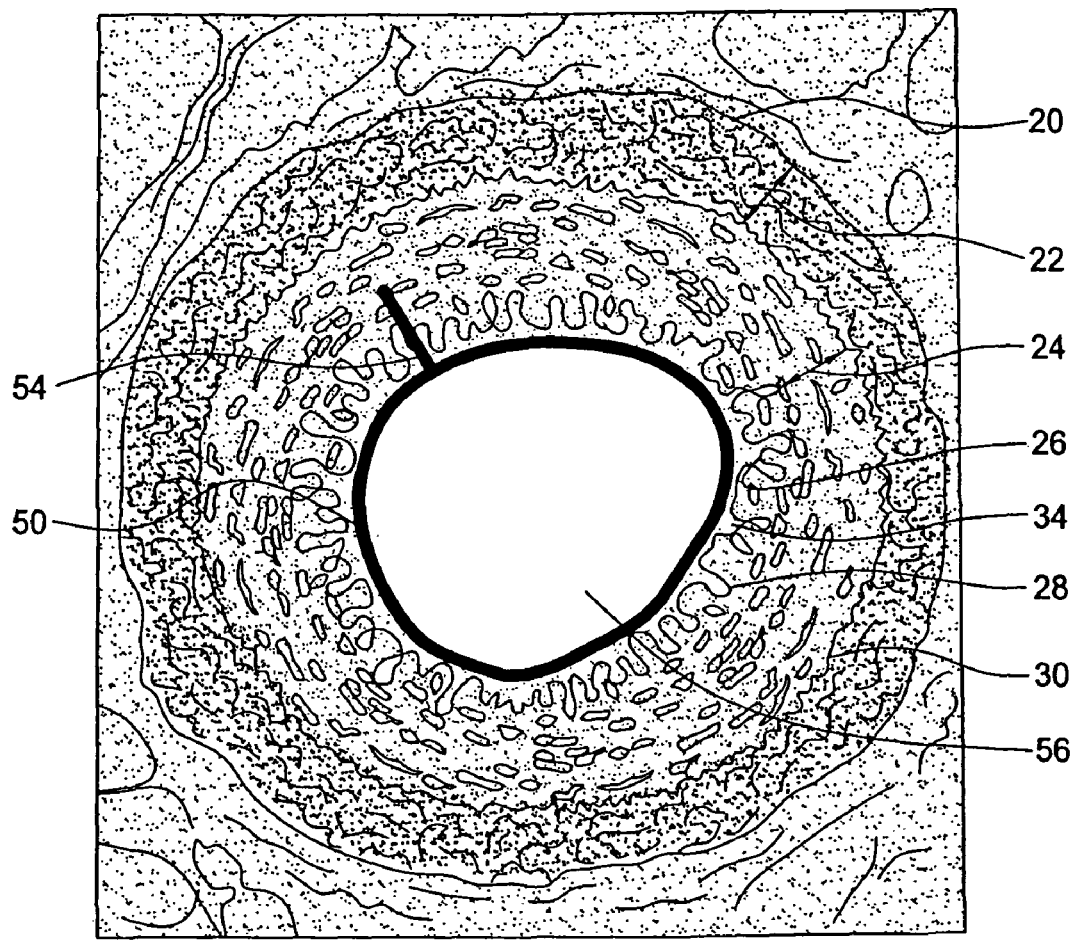
FIG. 3 is a partial sectional view of a blood vessel where skeletal myoblasts or myocytes may be delivered.

FIG. 3 shows a horizontal cross section of an artery. FIG. 3 shows an artery (20), having a tunica intima (26) adjacent to an internal or inner elastic lamina (28). The tunica media (24) in FIG. 3 is reduced in size, as compared to a normal artery, due to degeneration of the muscle and elastic fibers of the tunica media layer. Encircling the tunica media (24) is the outer or external elastic lamina (30), the tunica adventitia (22), and the outer elastic lamina (30). In addition to the cross section of the catheter (50), an area between the catheter (50) in the lumen (34) of the artery and the intima layer (26) is present, as well as the inner lumen of the catheter (56). Also, there is a delivery means (54) seen in cross section projecting from the catheter (50) into the tunica media (24).

In some procedures where vessel repair is necessarily extensive—particularly at aneurysmal sites—a stent graft is used, and a catheter may be tracked along side the stent to deliver the stem cells to the media of the vessel. Such stents are known in the art.

Figure 4:
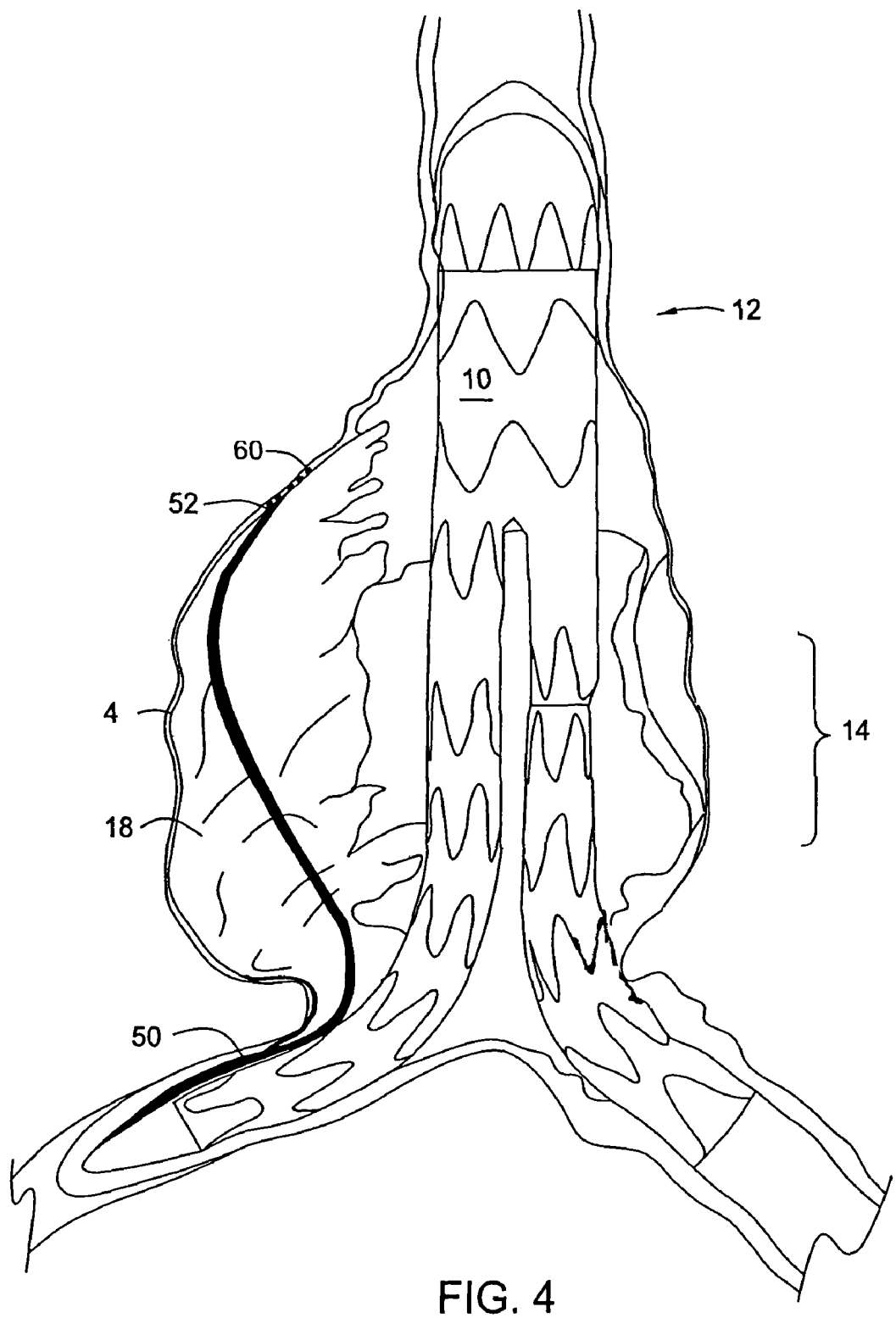
FIG. 4 is a partial sectional view of a descending aorta with a bifurcated stent graft placed therein, and a delivery catheter and stem cells delivered to the blood vessel wall of an aneurysmal sac.

FIG. 4 shows one embodiment of delivery of the myocytes or myoblasts involving the transluminal placement of a prosthetic arterial stent graft 10 positioned in an aorta 12. The stent spans, within the aorta 12, an aneurysmal portion 14 of the aorta 12. The aneurysmal portion 14 is formed due to a bulging of the aorta wall 04. As a result, an aneurysmal sac 18 is formed of distended vessel wall tissue. The stent graft 10 is positioned spanning the sac 18 providing both a passageway for blood flow through the aorta 12 and sealing of the aneurysmal portion 14 of the aorta 12 from additional blood flow from the aorta 12. In addition, FIG. 4 shows a portion of a catheter 30 tracked along side of the stent graft 10. The catheter 30 has a distal end 32 that resides in the aneurysmal wall 04 of the aorta 12. The myoblasts or myocytes 60 are delivered to the aneurysmal wall 04 through the distal end 52 of the catheter 50. As discussed, the cells delivered may or may not be bioengineered, and may or may not be accompanied by cellular scaffolding, delivery solutions and/or soluble bioactive molecules such as cytokines, growth factors, and angiogenic factors. The cells and other elements, if present, support or bolster the aneurysm, while providing the factors necessary to stimulate the growth of new tissue to continue to support the aneurysm.

EXAMPLES

Skeletal Muscle Myoblast Isolation

General anesthesia is induced with intravenous pentobarbital and maintained with 1% halothane administered through an endotracheal tube. Under sterile conditions, a longitudinal incision is made over the projection of the tibialis anterior muscle. A portion of the muscle is removed and placed in ice-cold saline solution. The operative wound is closed in layers.

Immediately following the explantation procedure, excessive connective tissue and fasciae are removed thoroughly from the specimen. The skeletal muscle obtained is rinsed with 70% ethyl alcohol for 30 seconds. The muscle is then rinsed with 150 mL of Hank's balanced salt solution and minced with scissors until fine pieces of muscle form a homogeneous mass. Muscle fragments are sedimented in conical 50-mL polypropylene tubes at 540 g for 1 minute. The supernatant is then discarded. This step is repeated twice more.

To digest the connective tissue, the specimen is incubated for 15 minutes at 37° C. with 1% collagenase and 0.2% type 1-S hyaluronidase in M199 solution supplemented with 5,000 IU/mL penicillin and 5,000 µg/mL streptomycin. The remaining muscle mass then is spun down at 540 g for 10 minutes.

The connective tissue elements released are aspirated and discarded with the supernatant. The muscle fragments are subjected to further enzymatic digestion using 1% pronase solution at 37° C. for 15 minutes to release the myoblasts. The obtained myoblasts are sedimented at 540 g for 10 minutes and only the supernatant containing released myoblasts is retained. Fetal bovine serum is added to the supernatant to halt enzymatic cleavage processes. The remaining tissue debris is separated from the cells by centrifugation at 775 g for 15 minutes. The collected cell pellet is washed and resuspended in the same manner four times.

To purify the cell culture from fibroblasts present in the final cell pellet, the density centrifugation method described by Yablonka-Reuveni and Nameroff in *Histochemistry*, 87: 27-38 (1987) is used. In brief, the cell suspension is layered on 20% Percoll, which itself rests on a 60% Percoll layer. The whole liquid structure is centrifuged at 15,000 g for 5 minutes. The cell layer obtained at the interface of the 20% and 60% Percoll concentrations consists mostly of myoblasts, whereas the majority of the fibroblasts and other cells are situated within the other layers at different levels. Retrieved myoblasts are counted on a cytometer.

The myoblasts are plated on 60-mm polystyrene tissue culture dishes, which are coated in advance with a layer of laminin to promote myoblast adherence to the bottom of the culture dish. The plating density can range from $5 \times 10^5$ to $7.5 \times 10^5$ cells per culture dish. Growth medium contains per 100 mL: 82 mL M199, 7.4 mL minimum essential medium, 10 mL fetal bovine serum, 5,000 IU/mL penicillin, 5,000 µg/mL streptomycin, 250 µL amphotericin B and 40 µL gentamicin. Medium is replaced every 24 to 48 hours and the myoblast cultures are maintained in 37° C. humidified atmosphere of 95% air with 5% $CO_2$.

Cardiomyocyte Enrichment

Using this approach, the generation of highly enriched cardiomyocyte cultures is quite simple. Undifferentiated ES cells are transfected with the MHC-neo$^r$/pGK-hygro$^r$ construct. Cells incorporating the DNA are enriched based on their resistance to hygromycin. Differentiation is then induced, and once evidence of cardiomyogenesis is observed (i.e., spontaneous contractile activity), the cultures are treated with geneticin (G418). Because the α-MHC promoter is only active in myocytes, only these cells express aminoglycoside phosphotransferase and survive G418 treatment. Although the example presented utilizes antibiotic resistance as the basis of the enrichment, a wide variety of analogous marker genes/enrichment protocols can be used (e.g., green fluorescent protein (GFP) targeted expression of cell surface markers, which could be used in conjunction with fluorescence-activated cell sorting (FACS) protocols, and the like).

The genetic enrichment approach has the advantage that very long-term cultures of differentiated myocytes can be generated, since nonmyocytes are eliminated from the culture. Moreover, the approach is easily amenable to gene transfer, either prior to differentiation or, alternatively, after the generation of differentiated cells.

Prior to transfection of ES cells, the selection cassette (pMHC-neo$^r$/PGK-hygro$^r$) is digested with XhoI/HindIII and the 8.8-kb fragment containing the entire MHC-neo$^r$/PGK-hygro$^r$ sequence is isolated using a Gene Clean kit. ES cells are routinely maintained in an undifferentiated state by culturing them in the ES growth medium (DMEM containing 15% heat-inactivated FBS, 0.1 mM nonessential amino acids, 2 mM glutamine, 50 U/mL penicillin, 50 µg/mL streptomycin, 0.1 mM 2-mercaptoethanol, and 103 U/mL LIF). The cells are dissociated using trypsin, counted, and $4\times10^6$ cells are resuspended in 0.8 mL of ES growth medium and then transferred into an electroporation chamber and left on ice.

MHC-neo$^r$/PGK-hygro$^r$ DNA (1 µg and 25 µg sonicated salmon testes DNA in a total volume of 70 µL) is sonicated, added to the cells, and left in the electroporation chamber on ice for 15 minutes. The cells are electroporated (180 V, 800 µF) and left on ice for 15 minutes, then plated in 100-mm Corning dishes ($6\times10^5$ cells/dish) in ES growth medium for 24 hours. The next day the growth medium is aspirated and the cells are switched to ES growth medium supplemented with 200 µg/mL hygromycin B. The medium is changed daily and the transfected cells are selected over a period of 7 days. Cells may be trypsinized and replated into new dishes if a plate becomes confluent.

After seven days of hygromycin selection, the cells are dissociated using trypsin and plated at a density of $4\times10^6$ cells in a 100-mm bacterial Petri dish in 10 mL of differentiation medium A (DMEM containing 15% heat-inactivated FBS, 0.1 mM nonessential amino acids, 2 mM glutamine, 50 U/mL penicillin, 50 µg/mL streptomycin, and 0.1 mM 2-mercaptoethanol). Cells will grow in suspension under these conditions. The cells are supplemented with 5 mL of differentiation medium A on the next day, to facilitate EB formation. On the third day, the medium containing EBs is transferred using a 10-mL pipet into a sterile 50-mL cell culture tube and the EBs are allowed to settle by gravity. The medium is aspirated and the EBs are resuspended in 10 mL of fresh differentiation medium A, and plated in a new bacterial Petri dish. The cells are supplemented with 5 mL of differentiation medium A on the next day.

EBs are collected on the fifth day by gravity and resuspended in 10 mL of differentiation medium B (DMEM containing 20% heat-inactivated FBS, 0.1 mM nonessential amino acids, 2 mM glutamine, 50 U/mL penicillin, 50 µg/mL streptomycin, and 0.1 mM 2-mercaptoethanol). The EBs are plated in 100-mm Corning cell culture dishes at different dilutions (1:2, 1:5, 1:10, etc). The medium is changed daily and regions of cardiogenesis can be identified readily by the presence of spontaneous contractile activity within 4-6 days of EB attachment.

For enrichment of cardiomyocyte restricted lineages, cultures exhibiting spontaneous contractile activity are grown in differentiation medium C (DMEM containing 20% heat-inactivated FBS, 0.1 mM nonessential amino acids, 2 mM glutamine, 50 U/mL penicillin, 50 µg/mL streptomycin, 0.1 mM 2-mercaptoethanol, and 200 µg/mL G418). Cultures can be grown in differentiation medium C for as long as required to eliminate nonmyocytes.

Skeletal Muscle Cell Differentiation

Differentiation protocols for the development of ES cells into skeletal muscle have been well established, allowing investigators to analyze developmental processes during differentiation, study effects of differentiation factors on embryogenesis, and establish strategies for cell and tissue therapy. Described in this example is a method of cultivating undifferentiated ES cells on a feeder layer, with subsequent differentiation.

To culture a feeder layer, embryos are removed from a mouse pregnant for 15 to 17 days. The embryos are rinsed in PBS, and the placenta and fetal membranes, head, liver, and heart are removed. The carcasses are then rinsed in trypsin solution. The embryonic tissue is then rinsed in 5 mL of fresh trypsin solution, transferred to an Erlenmeyer flask containing a stir bar and stirred on magnetic stirrer for 25 to 45 minutes. The suspension is filtered through a sieve or a screen, 10 mL of culture medium 1 (85 mL DMEM, 15 mL FCS, 1 mL 200 mM L-glutamine, 1 mL βME, 1 mL nonessential amino acids) is added, and the suspension is and centrifuged.

The pellet is then resuspended in about 3 mL of culture medium 1 (85 mL DMEM, 15 mL FCS, 1 mL 200 mM L-glutamine, 1 mL βME, 1 mL nonessential amino acids), plated on 100-mm tissue culture plates (about $2\times106$ cells/100 mm-dish) containing 10 mL culture medium I, and incubated at 37° C. and 5% $CO_2$ for 24 hours. The medium is changed as needed to remove debris, erythrocytes, and unattached cellular aggregates, and the culture is incubated for an additional 1 to 2 days.

To pass the primary culture of mouse embryonic fibroblasts, the culture is split 1:2 to 1:3 onto 100-mm tissue culture plates, and grown in culture medium I (85 mL DMEM, 15 mL FCS, 1 mL 200 mM L-glutamine, 1 mL BME, 1 mL nonessential amino acids) for 1 to 3 days. The cells in passages 2-4 are most suitable as feeder layer for undifferentiated ES cells. Next, the feeder layer cells are incubated with MC buffer (300 µL of 0.2 mg/mL mitomycin C in 6 mL PBS) for 2 to 3 hours, then the MC solution is aspirated and the cells are washed three times with PBS, trypsinized and replated onto new gelatin (0.1%)-treated microwell plates or to Petri dishes. Feeder layer cells prepared 1 day before ES cell subculture are optimal.

For the development of ES cells into differentiated phenotypes, cells must be cultivated in 3-dimensional aggregates called embryoid bodies (EBs) by the hanging drop method, by mass culture, or by differentiation in methylcellulose. The differentiation of cardiac and skeletal cells requires different conditions, and these may vary for the particular ES cell line used. In this example, a differentiation protocol utilizing the hanging drop method is described.

A cell suspension is prepared containing a defined ES cell number of, for example, 600 cells in 20 µL of differentiation medium (80 mL DMEM, 20 mL FCS, 1 mL 200 mM L-glutamine, 1 mL BME, 1 mL nonessential amino acids). 20 µL drops (n=50-60) of the ES cell suspension are placed on the lids of 100-mm bacteriological Petri dishes containing 10 mL PBS. The ES cells are cultivated in hanging drops for 2 days, where the cells will aggregate and form one EB per drop.

The aggregates are rinsed carefully from the lids with 2 mL of medium, transferred into a 60-mm bacteriological Petri dish with 5 mL of differentiation medium, and cultivation is continued in suspension for 2 to 5 days until the time of plating.

A single EB is transferred into each well of gelatin (0.1%)-coated microwell plates for morphological analysis, or transferred 20-40 EBs per dish onto 60-mm tissue culture dishes containing 4 coverslips (10×10 mm) for immunofluorescence, or 15 to 20 EBs onto 60-mm tissue culture dishes for reverse transcription PCR (RT-PCR) analysis of EB outgrowths. The medium during EB differentiation is changed every second or third day.

To characterize the EB outgrowths morphologically, the percentage of EBs is calculated with the specific differentiated cell type (from EBs of at least 48 wells) or the amount of the differentiated cell type is calculated as a percentage of the outgrowth area of each EB.

While the present invention has been described with reference to specific embodiments, it should be understood by those skilled in the art that various changes may be made and equivalents may be substituted without departing from the true spirit and scope of the invention. In addition, many modifications may be made to adapt a particular situation, material, or process to the objective, spirit and scope of the present invention. All such modifications are intended to be within the scope of the invention.

All references cited herein are to aid in the understanding of the invention, and are incorporated in their entireties for all purposes.

The invention claimed is:

1. A method of providing therapy to a blood vessel wall at an aneurysmal site, said therapy comprising the steps of:
    obtaining self-derived skeletal muscle;
    isolating cells from the self-derived skeletal muscle wherein the isolated cells are selected from the group consisting of myocytes, myoblasts, and a combination thereof; and
    delivering said isolated cells directly to the blood vessel wall at the aneurysmal site by a delivery means selected from the group consisting of (1) a cell-associated implant selected from the group consisting of a carrier or scaffold, cells encapsulated in biodegradable microspheres or capsules, and an implanted stent and a wrap comprised of cells embedded within a matrix or scaffold, applied either periadventially or intralumenally and (2) injection of cells directly into the vessel wall at the aneurysmal site;
    wherein said therapy results in one or more of inducing new muscle growth at the aneurysmal site, reducing inflammation at the aneurysmal site, regenerating extracellular matrix components in the medial or adventitial blood vessel layers at the aneurysmal site or inhibiting matrix metalloproteinases.

2. The method of claim 1, wherein the cells are isolated by at least one of growth in selective medium, growth in differentiation medium, by density centrifugation, fluorescence activated cell sorting or by magnetic activated cell sorting.

3. The method of claim 2, wherein the cells are isolated by assaying for α-cardiac myosin heavy chain peptide, myosin light chain isoform 2V, NKX2.5, Myf5, myogenin, MyoD, Myf6, or M-Cadherin.

4. The method of claim 1, further comprising the step of expansion of the isolated cells by in vitro culturing.

5. The method of claim 1, further comprising the step of combining the cells with scaffolding material after the obtaining step.

6. The method of claim 5, wherein the scaffolding material is biodegradable.

7. The method of claim 5, wherein the scaffolding material is a gel.

8. The method of claim 7, wherein the gel is a stimuli-responsive gel.

9. The method of claim 8, wherein the stimuli-responsive gel is biodegradable.

10. The method of claim 1, wherein the isolated cells are delivered directly to the aneurysm site by injection of the cells into the vessel wall using a device selected from the group consisting of a catheter, a cannula, and a microneedle.

11. The method of claim 1, wherein the isolated cells to be delivered further comprise a carrier compound.

12. The method of claim 11, wherein the carrier compound is sterile water, normal saline or culture medium, with or without bioactive agents.

13. The method of claim 1, wherein the cells isolated are myoblasts.

14. The method of claim 13, wherein the myoblasts are isolated from the tibialis anterior muscle.

15. The method of claim 13, wherein the myoblasts are isolated by at least one of growth in selective medium, by density centrifugation, fluorescence activated cell sorting or by magnetic activated cell sorting.

16. The method of claim 15, wherein the myoblasts are isolated by assaying for α-cardiac myosin heavy chain peptide, myasin light chain isoform 2V, NKX2.5, Myf5, myogenin, MyoD, Myf6, or M-Cadherin.

17. The method of claim 13, further comprising the step of modifying the myoblasts after the isolating step.

18. The method of claim 17, wherein the modifying step is accomplished by genetic engineering.

19. The method of claim 18, wherein the myoblasts are genetically engineered to produce at least one cellular factor selected from the group of collagen I, collagen III, elastin, cytokines, growth factors, metalloproteinase inhibitors, inhibitors of inflammation, vitamin A, vitamin C or angiogenic factors.

20. The method of claim 17, wherein the modifying step is in vitro culture expansion of the myoblasts.

21. The method of claim 13, further comprising the step of combining the myoblasts with scaffolding material after the isolating step.

22. The method of claim 21, wherein the scaffolding material is biodegradable.

23. The method of claim 22, wherein the scaffolding material promotes healing of the aneurysmal site.

24. The method of claim 22, wherein the scaffolding material is a gel.

25. The method of claim 24, wherein the gel is a stimuli-responsive gel.

26. The method of claim 25, wherein the stimuli-responsive gel is biodegradable.

27. The method of claim 23, wherein the myoblasts are genetically engineered to produce at least one cellular factor selected from the group of collagen I, collagen III, elastin, cytokines, growth factors, metalloproteinase inhibitors, inflammation, vitamin A, vitamin C or angiogenic factors.

28. The method of claim 13, wherein the delivery means is a catheter, cannula, microneedle, or through a wrap comprising of cells embedded within a matrix or scaffold, applied either periadventially or intralumenally.

29. The method of claim 13, wherein the myoblasts to be delivered further comprise a carrier compound.

30. The method of claim 29, wherein the carrier compound is sterile water, normal saline or culture medium, with or without bioactive agents.

* * * * *